United States Patent
Ikemoto et al.

(10) Patent No.: US 7,605,286 B2
(45) Date of Patent: Oct. 20, 2009

(54) HYDROXY-PROTECTING REAGENT AND METHOD OF PROTECTING HYDROXY WITH THE SAME

(75) Inventors: Tetsuya Ikemoto, Osaka (JP); Yosuke Watanabe, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/567,150

(22) PCT Filed: Jun. 23, 2004

(86) PCT No.: PCT/JP2004/009215

§ 371 (c)(1),
(2), (4) Date: Oct. 2, 2006

(87) PCT Pub. No.: WO2005/014508

PCT Pub. Date: Feb. 17, 2005

(65) Prior Publication Data

US 2007/0155983 A1 Jul. 5, 2007

(30) Foreign Application Priority Data

Aug. 6, 2003 (JP) .............................. 2003-288300
Mar. 18, 2004 (JP) .............................. 2004-079061

(51) Int. Cl.
*C07C 69/66* (2006.01)
*C07C 43/20* (2006.01)

(52) U.S. Cl. ..................... 560/179; 568/592; 568/596; 568/604; 568/662

(58) Field of Classification Search ..................... None
See application file for complete search history.

(56) References Cited

U.S. PATENT DOCUMENTS 5,739,100 A * 4/1998 Horino et al. .................. 512/25

FOREIGN PATENT DOCUMENTS

WO    WO 94/01414 A    1/1994

OTHER PUBLICATIONS

Database WPI Week 198907, Derwent Publications Ltd., AN 1989-052002, XP002426560 (JP64 003124 A, Okahara M., Jan. 6, 1989).
L.M. Beauchamp et al., "Effect of Acrylic Pyrimidines Related to 9-[(1,3-Dihydroxy-2-propoxy)methyl] guanine on Herpesviruses", J. Med. Chem. Jan. 1988, vol. 31, No. 1, pp. 144-149 (scheme I).
X-P Gu et al., "2-(chloramethyl)-3, 4-dioxahex-1-ene. An Effective Acetonylating Reagent", J. Org. Chem., 1987, vol. 52, No. 15, pp. 3192-3196 (scheme I).
T.W. Greene et al., "Protective Groups in Organic Synthesis Third Edition", New York, John Wiley & Sons, Inc., 1999, ISBN 0-471-16019-9, pp. 27-29.

* cited by examiner

*Primary Examiner*—Rosalynd Keys
(74) *Attorney, Agent, or Firm*—Foley & Lardner LLP

(57) ABSTRACT

The present invention relates to a method of protecting a hydroxyl group, which includes reacting a hydroxyl group-containing compound with a compound represented by the formula (I):

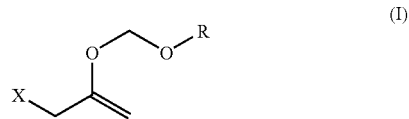

wherein R is a phenyl group optionally having substituent(s), an alkyl group optionally having substituent(s) or a benzyl group optionally having substituent(s), and X is a halogen atom, in the presence of an acid catalyst to substitute the hydrogen atom of the hydroxyl group of the hydroxyl group-containing compound with a protecting group represented by the formula (II):

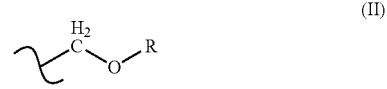

wherein R is as defined above. The present invention provides a method capable of introducing an acetal type protecting group into a hydroxyl group under mild conditions, and a protecting reagent therefor and a method of producing the protecting reagent.

5 Claims, No Drawings

HYDROXY-PROTECTING REAGENT AND METHOD OF PROTECTING HYDROXY WITH THE SAME

TECHNICAL FIELD

The present invention relates to a protecting reagent useful for protecting a hydroxyl group with an acetal type protecting group such as methoxymethyl group and the like and a method of protecting a hydroxyl group with the protecting reagent.

BACKGROUND ART

In the organic synthesis of a compound having a functional group such as a hydroxyl group, an amino group and the like, appropriate protection of the functional group is important for synthesis tactics.

Acetal type protecting group represented by the formula (II): —CH$_2$OR (II) wherein R is a phenyl group optionally having substituent(s), an alkyl group optionally having substituent(s) or a benzyl group optionally having substituent(s), which is exemplified by a methoxymethyl group, an ethoxymethyl group, a methoxyethoxymethyl group and the like, hereinafter to be also referred to as protecting group (II), is used as a hydroxyl-protecting group. Since the group is stable under various reaction conditions and can be easily deprotected under weak acidic conditions, it is highly valuable for use as a hydroxyl-protecting group.

As a method of protecting a hydroxyl group with protecting group (II), 1) a method comprising reaction by adding dropwise alkoxymethyl chloride in the presence of a small excess of diisopropylethylamine and 2) a method comprising reacting a large excess of dialkoxymethane with heating in the presence of a strong acid catalyst are known (Protective Groups in organic Synthesis, 3rd Edition, Wiley Interscience Publication, John Wiley & Sons, Inc., 1999, p. 27-49).

However, the reaction system of 1) is associated with problems in that it requires basic conditions and cannot be employed for the protection of alcohol unstable to base, and that highly toxic alkoxymethyl chloride is used. The reaction system of 2) is associated with problems in that it requires strong acidic conditions and cannot be employed for the protection of alcohol unstable to acid, that it is uneconomical due to the use of a large excess of dialkoxymethane, and further that the reaction tends to be complicated because it involves equilibrium reaction and the like.

In view of the above, a method capable of introducing protecting group (II) under mild conditions into general alcohols including alcohol unstable to acid or base has been desired.

DISCLOSURE OF THE INVENTION

An object of the present invention is to provide a method capable of introducing an acetal type protecting group into a hydroxyl group under mild conditions and a protecting reagent therefor, and further, a method capable of producing the protecting reagent safely and conveniently.

The present inventors have conducted intensive studies in an attempt to solve the above-mentioned problems and found a reagent capable of introducing protecting group (II) into a hydroxyl group in a high yield under mild reaction conditions such as weak acidic ones. They have further found a method capable of producing the protecting reagent more safely and conveniently than conventional methods, which resulted in the completion of the present invention.

Accordingly, the present invention provides the following.

(1) A method of protecting a hydroxyl group, which comprises reacting a hydroxyl group-containing compound with a compound represented by the formula (I):

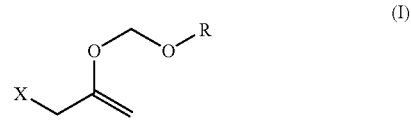

wherein R is a phenyl group optionally having substituent(s), an alkyl group optionally having substituent(s) or a benzyl group optionally having substituent(s), and X is a halogen atom (hereinafter to be also referred to as compound (I)), in the presence of an acid catalyst to substitute the hydrogen atom of the hydroxyl group of the hydroxyl group-containing compound with protecting group (II).

(2) The method of the above-mentioned (1), wherein R is a phenyl group optionally having substituent(s) or an alkyl group optionally having substituent(s).

(3) The method of the above-mentioned (2), wherein R is an alkyl group.

(4) The method of any one of the above-mentioned (1) to (3), wherein the acid catalyst is pyridinium p-toluenesulfonate or p-toluenesulfonic acid.

(5) The method of the above-mentioned (4), wherein the acid catalyst is pyridinium p-toluenesulfonate.

(6) A hydroxyl group-protecting reagent which comprises compound (I).

(7) The reagent of the above-mentioned (6), wherein R is a phenyl group optionally having substituent(s) or an alkyl group optionally having substituent(s).

(8) The reagent of the above-mentioned (7), wherein R is an alkyl group.

(9) The reagent of the above-mentioned (8), wherein R is a methyl group.

(10) A method of producing compound (I) which comprises the following Step 1 and Step 2;

Step 1: reacting a compound represented by the formula (III):

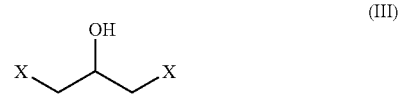

wherein X is as defined above (hereinafter to be also referred to as compound (III)), with a compound represented by the formula (IV):

wherein R is as defined above (hereinafter to be also referred to as compound (IV)), to give a compound represented by the formula (V):

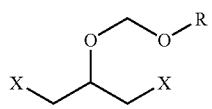

(V)

wherein each symbol is as defined above (hereinafter to be also referred to as compound (V));

Step 2: reacting the obtained compound (V) in the presence of a base to give compound (I).

(11) The method of the above-mentioned (10), wherein R is a methyl group.

(12) A method of producing compound (V) which comprises reacting compound (III) with compound (IV).

(13) The method of the above-mentioned (12), wherein R is a methyl group.

According to the hydroxyl group-protecting reagent and the method of protecting a hydroxyl group of the present invention, a hydroxyl group can be protected with protecting group (II) under mild reaction conditions such as weak acidic conditions and the like. Consequently, a hydroxyl group of a hydroxyl group-containing compound unstable under strong basic conditions or strong acidic conditions can be protected with protecting group (II), and therefore, this invention is highly useful for synthesis tactics. Moreover, this invention is advantageous in that it can also be performed safely because alkoxymethyl chloride, which is highly toxic and requires careful attention during handling, is not necessary.

According to the above-mentioned (10)-(13), moreover, a method of producing compound (I), which is useful as the hydroxyl group-protecting reagent of the present invention as well as an acetonylating reagent, safely and conveniently without using high toxic alkoxymethyl chloride, is provided.

DETAILED DESCRIPTION OF THE INVENTION

The present invention is explained in detail in the following.

1. Definition of Symbols

As the "halogen atom" for X, a fluorine atom, a chlorine atom, a bromine atom and an iodine atom can be mentioned. Preferred are a chlorine atom and a bromine atom and more preferred is a chlorine atom.

As the "alkyl group" of the "alkyl group optionally having substituent(s)" for R, a linear or branched chain alkyl group having 1 to 12 carbon atoms, preferably 1 to 8 carbon atoms, more preferably 1 to 3 carbon atoms, such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, nonyl, decyl, undecyl, dodecyl and the like can be mentioned. Preferred are methyl, ethyl, propyl and isopropyl, and more preferred are methyl and ethyl.

The alkyl group optionally has substituent(s) at a substitutable position(s) and as the substituents, a halogen atom (those recited in the above-mentioned can be mentioned), an alkoxy group (a linear or branched chain alkoxy group having 1 to 12 carbon atoms, preferably 1 to 4 carbon atoms, more preferably 1 to 3 carbon atoms, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, nonyloxy, decyloxy, undecyloxy, dodecyloxy etc.) and the like can be mentioned, with preference given to methoxy and ethoxy. The number of the substituents is not particularly limited, and 1 to 3 is preferable, where the substituents may be the same or different.

As the substituents of the "phenyl group optionally having substituent(s)" or "benzyl group optionally having substituent(s)" for R, those recited as the substituents of the abovementioned alkyl group and an alkyl group (the alkyl group is as defined above) can be mentioned. The number of the substituents is not particularly limited, and 1 to 3 is preferable, where the substituents may be the same or different.

R is preferably an "alkyl group optionally having substituent(s)" or a "phenyl group optionally having substituent(s)", more preferably an "alkyl group optionally having substituent(s)", more preferably an "alkyl group", and still more preferably a methyl group.

2. Hydroxyl Group-Containing Compound

A hydroxyl group-containing compound is not particularly limited and can be used for the present invention as long as it is an organic compound having hydroxyl group(s) in a molecule, and may have a phenolic hydroxyl group or may be an aliphatic alcohol, and may be a primary alcohol, secondary alcohol or tertiary alcohol. For example, an alcohol compound represented by following formula (A):

(A)

wherein $R^1$, $R^2$ and $R^3$ are the same or different and each is a hydrogen atom, an alkoxycarbonyl group, an acyl group, an alkyl group optionally having substituent(s), a cycloalkyl group optionally having substituent(s), an alkenyl group optionally having substituent(s), an alkynyl group optionally having substituent(s), an aryl group optionally having substituent(s), an aralkyl group optionally having substituent(s), a heteroaryl group optionally having substituent(s) and the like, or $R^1$ and $R^2$ optionally form, together with the carbon atom they are bonded to, a homocycle or a heterocycle, each optionally having substituent(s) (hereinafter to be also referred to as alcohol (A)) can be preferably used but the hydroxyl group-containing compound is not limited thereto.

As the "alkoxycarbonyl group" in alcohol (A), an alkoxycarbonyl group wherein the alkyl moiety is the alkyl group exemplified for R. For example, methoxycarbonyl, ethoxycarbonyl, propoxycarbonyl, isopropoxycarbonyl, butoxycarbonyl, isobutoxycarbonyl, tert-butoxycarbonyl and the like can be mentioned.

As the "acyl group" in alcohol (A), an acyl group having 2 to 5 carbon atoms, such as acetyl, propionyl, isopropionyl, butyryl, isobutyryl, pivaloyl and the like can be mentioned.

As the "alkyl group" of the "alkyl group optionally having substituent(s)" in alcohol (A), those recited as the alkyl group defined for R can be mentioned.

As the "cycloalkyl group" of the "cycloalkyl group optionally having substituent(s)" in alcohol (A), a cycloalkyl group having 3 to 8 carbon atoms, such as cyclopropyl, cyclobutyl, cyclopentyl, cyclohexyl, cycloheptyl, cyclooctyl and the like can be mentioned.

As the "alkenyl group" of the "alkenyl group optionally having substituent(s)" in alcohol (A), a linear or branched alkenyl group having 2 to 12 carbon atoms, such as ethenyl, 1-propenyl, allyl, 1-methyl-2-propenyl, 1-butenyl, 2-butenyl, 3-butenyl, 1-pentenyl, 2-pentenyl, 1-hexenyl, 2-hexenyl, 1-heptenyl, 2-heptenyl, 1-octenyl, 2-octenyl, 1-nonenyl, 2-nonenyl, 1-decenyl, 2-decenyl and the like can be mentioned.

As the "alkynyl group" of the "alkynyl group optionally having substituent(s)" in alcohol (A), a linear or branched chain alkynyl group having 2 to 12 carbon atoms, such as ethynyl, 1-propynyl, 2-propynyl, 1-methyl-2-propynyl, 1-butynyl, 2-butynyl, 3-butynyl, 1-pentynyl, 2-pentynyl, 1-hexynyl, 2-hexynyl, 1-heptynyl, 2-heptynyl, 1-octynyl, 2-octynyl, 1-nonynyl, 2-nonynyl, 1-decynyl, 2-decynyl and the like can be mentioned.

As the "aryl group" of the "aryl group optionally having substituent(s)" in alcohol (A), an aryl group having 6 to 20 carbon atom, such as phenyl, 1- or 2-naphthyl, biphenyl, binaphthyl and the like can be mentioned.

As the "aralkyl group" of the "aralkyl group optionally having substituent(s)" in alcohol (A), for example, an aralkyl group formed by substituting any position of the "alkyl group" defined above with the "aryl group" defined above. For example, benzyl, 1- or 2-phenethyl, 1-, 2- or 3-phenylpropyl, 1- or 2-naphthylmethyl, benzhydryl, trityl and the like can be mentioned.

As the "heteroaryl group" of the "heteroaryl group optionally having substituent(s)" in alcohol (A), such as a 5- to 7-membered aromatic heterocyclic group containing, besides carbon atoms, 1 to 4 hetero atoms selected from an oxygen atom, a sulfur atom and a nitrogen atom, a fused heterocyclic group thereof and the like can be mentioned. For example, 2- or 3-thienyl, 2- or 3-furyl, 1-, 2- or 3-pyrrolyl, 1-, 2-, 4- or 5-imidazolyl, 2-, 4- or 5-oxazolyl, 2-, 4- or 5-thiazolyl, 1-, 3-, 4- or 5-pyrazolyl, 3-, 4- or 5-isoxazolyl, 3-, 4- or 5-isothiazolyl, 1,2,4-triazol-1,3,4 or 5-yl, 1,2,3-triazol-1,2 or 4-yl, 1H-tetrazol-1 or 5-yl, 2H-tetrazol-2 or 5-yl, 2-, 3- or 4-pyridyl, 2-, 4- or 5-pyrimidinyl, 1-, 2-, 3-, 4-, 5-, 6- or 7-indolyl, 2-, 3-, 4-, 5-, 6- or 7-benzofuryl, 2-, 3-, 4-, 5-, 6- or 7-benzothienyl, 1-, 2-, 4-, 5-, 6- or 7-benzimidazolyl, 2-, 3-, 4-, 5-, 6-, 7- or 8-quinolyl, 1-, 3-, 4-, 5-, 6-, 7- or 8-isoquinolyl and the like can be mentioned.

As the homocycle optionally having substituent(s), which are optionally formed by $R^1$ and $R^2$ together with the carbon atom they are bonded to, an aliphatic homocycle having 3 to 8 carbon atoms, such as cyclopropane, cyclobutane, cyclopentane, cyclohexane, cycloheptane, cyclooctane and the like can be mentioned.

As the heterocycle optionally having substituent(s), which are optionally formed by $R^1$ and $R^2$ together with the carbon atom they are bonded to, an aliphatic heterocycle having 3 to 7 carbon atoms, such as tetrahydropyran, tetrahydrofuran, pyrrolidine, piperidine, morpholine, thiomorpholine, piperazine, tetrahydrothiophene, tetrahydrothiopyran and the like can be mentioned.

The above-mentioned "alkyl group", "cycloalkyl group", "alkenyl group", "alkynyl group", "aryl group", "aralkyl group", "heteroaryl group", "homocycle" and "heterocycle" optionally have substituent(s) at substitutable position(s). The substituents are exemplified by, but not limited to, an alkyl group (exemplified by those defined above, except the substituents for the alkyl group, alkenyl group and alkynyl group), a halogen atom (exemplified by those defined above), an alkoxycarbonyl group (exemplified by those defined above), an acyl group (exemplified by those defined above), an oxo, a nitro group, a cyano group and the like. The number of the substituents is not particularly limited, and 1 to 4 is preferable, where the substituents may be the same or different.

Alcohol (A) is preferably a compound wherein any one of $R^1$, $R^2$ and $R^3$ is a hydrogen atom, namely, a secondary alcohol or a tertiary alcohol in view of good yield, and more preferably a secondary alcohol.

Of alcohol (A), since optically active alcohol, β-hydroxyester and the like, such as synthetic intermediates for pharmaceutical products (e.g., D or L-lactate, (S) or (R)-β-hydroxy-γ-butyrolactone, (S) or (R)-4-chloro-3-hydroxybutanoate, (S) or (R)-3-hydroxytetradecanoate etc.) are particularly unstable under strong basic condition or strong acid conditions and susceptible to racemization, elimination reaction and the like, the protection method of the present invention can be preferably applied thereto, which can be performed under mild reaction conditions such as weak acidic conditions and the like.

Furthermore, the protection method of the present invention can be preferably used, as a hydroxyl group-containing compound, for natural products such as saccharide, hydroxyl group-containing amino acids (serine, tyrosine etc.), peptides containing the amino acid, nucleic acids and the like, and synthetic intermediates thereof.

3. Protection Method of Hydroxyl Group

The method of protecting the hydroxyl group of the present invention is achieved, for example, by reacting a hydroxyl group-containing compound with compound (I) as a hydroxyl group-protecting reagent in a solvent in the presence of an acid catalyst to substitute the hydrogen atom of the hydroxyl group of the hydroxyl group-containing compound with protecting group (II). The order of addition of the reagents is not particularly limited and respective reagents may be added sequentially or simultaneous.

While compound (I) is not particularly limited as long as it contains R and X defined above, 2-(chloromethyl)-3,5-dioxahexa-1-ene is preferable since it is easily available.

As mentioned above, the hydroxyl group-containing compound is not particularly limited but aliphatic secondary alcohols and tertiary alcohols are preferable, and secondary alcohols are more preferable, since the yield is high.

As the acid catalyst to be used, for example, pyridinium p-toluenesulfonate, p-toluenesulfonic acid, benzenesulfonic acid, methanesulfonic acid, trifluoromethane sulfonic acid, acidic ion exchange resin and the like can be mentioned, and pyridinium p-toluenesulfonate and p-toluenesulfonic acid are preferable. In view of the applicable weak acidic mild reaction conditions, pyridinium p-toluenesulfonate is preferable, and in view of the short reaction time, p-toluenesulfonic acid is preferable. Thus, a suitable acid catalyst can be appropriately selected in consideration of the stability of the hydroxyl group-containing compound and producibility.

The amount of compound (I) to be used is preferably 0.9 mol to 1.5 mol, more preferably 1.0 mol to 1.3 mol, per 1 mol of the hydroxyl group-containing compound.

While the amount of the acid catalyst to be used varies depending on the acidity of the acid catalyst to be used, it is preferably 0.0001 mol to 0.5 mol, more preferably 0.001 mol to 0.1 mol, per 1 mol of the hydroxyl group-containing compound. While the reaction can be carried out even when the amount of the acid catalyst to be used is outside this range, when the amount is smaller than this range, the reaction tends to be slow, and when the amount is greater than this range, the side reaction may proceed.

The solvent to be used is not particularly limited as long as it does not inhibit the reaction and, for example, acetonitrile, benzotrifluoride, tetrahydrofuran (THF), dichloromethane, toluene, chlorobenzene, methyl tert-butyl ether and the like can be used alone or in a mixture, with preference given to acetonitrile and benzotrifluoride. When a mixed solvent is to be used, the solvents may be mixed at any ratio.

The amount of the solvent to be used is preferably within the range of 1 L to 50 L per 1 kg of the hydroxyl group-containing compound.

The reaction temperature is generally −20° C. to 100° C., preferably 0° C. to 50° C. The reaction time is generally 10 min to 14 days, preferably 10 min to 240 hr, more preferably 10 min to 60 hr.

The hydroxyl group-containing compound in which the hydroxyl group is protected can be isolated and purified by a conventional method after the completion of the reaction. For example, water, aqueous sodium hydrogencarbonate solution and the like is added to the reaction mixture, the mixture is extracted with an organic solvent, and the organic layer is concentrated to isolate a hydroxyl group-containing compound in which the hydroxyl group is protected. The compound can be further purified by a conventional purification method, such as recrystallization, silica gel column chromatography, distillation under reduced pressure and the like.

The protecting group (II) of the thus-obtained hydroxyl group-containing compound in which the hydroxyl group is protected can be eliminated by a known method, such as the method described in Protective Groups in Organic Synthesis, 3rd Edition, Wiley Interscience Publication, John Wiley & Sons, Inc., 1999, p. 27-49.

4. Production Method of Compound (I)

In the present invention, compound (I) to be used as a hydroxyl group-protecting reagent is known to be a useful acetonylating reagent for the production of pharmaceutical agents, agricultural chemicals and the like (see Journal of Organic Chemistry, 1987, vol. 52, p. 3192-3196 and Journal of Organic Chemistry, 1986, vol. 51, p. 5425-5427), and a compound wherein R is methyl and X is a chlorine atom is particularly known as the Okahara's reagent.

Compound (I) may be a commercially available product, or can be synthesized by the production method represented by the following scheme 1 (see Journal of Organic Chemistry, 1986, vol. 51, p. 5425-5427).

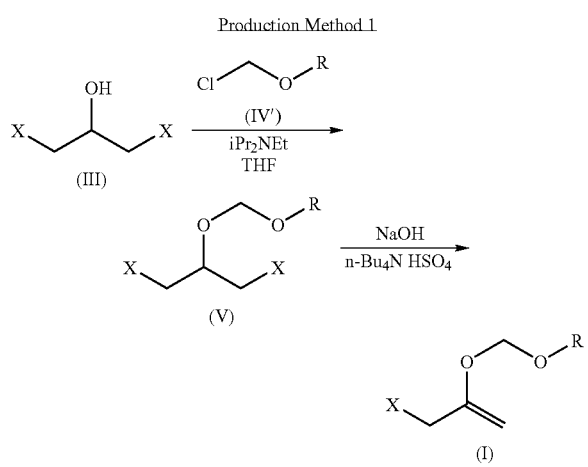

wherein each symbol is as defined above.

In Production Method 1, however, highly toxic alkoxymethyl chloride represented by the formula (IV') is used for the production of compound (V) (see Bulletin of the Chemical Society of Japan, 1987, vol. 60, p. 397-398). For industrial production of compound (I), careful production in a facility having a harm removing equipment is required, which reduces the merit of the above-mentioned protection method of hydroxyl group free of the use of alkoxymethyl chloride.

Therefore, the method of producing compound (I) according to Production Method 2 represented by the following scheme, which the present inventors propose, is preferable because compound (I) can be produced safely and conveniently.

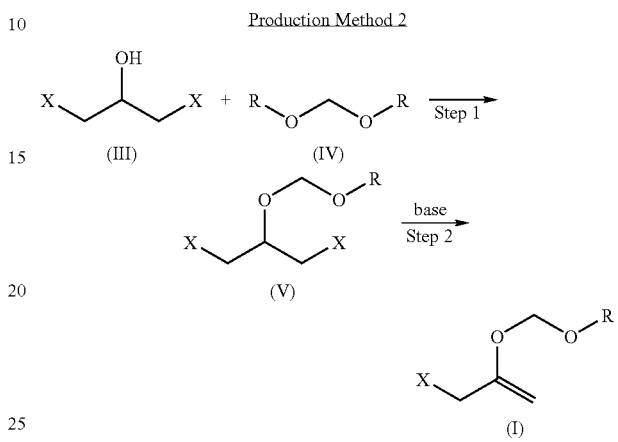

wherein each symbol is as defined above.

In Production Method 2, compound (V) can be produced by reacting compound (III) with low toxic compound (IV), instead of highly toxic alkoxymethyl halide requiring caution in handling, and compound (I) can be produced by treating compound (V) with a base to perform dehydrohalogenation. As mentioned above, since Production Method 2 does not require use of alkoxymethyl halide having high toxicity, compound (I) can be produced more safely and conveniently than Production Method 1.

Production Method 1 and Production Method 2 are explained in the following.

4-1. Production Method 1

In Production Method 1, compound (I) can be synthesized by Step 1 of reacting compound (III) with a compound represented by the formula (IV') (hereinafter to be also referred to as compound (IV')) in tetrahydrofuran (THF) in the presence of N,N-diisopropylethylamine to give compound (V) and then Step 2 of reacting compound (V) with sodium hydroxide in the presence of a phase transfer catalyst such as tetra-n-butylammonium hydrogensulfate.

Compound (IV') is used within the range of 0.8 mol to 1.5 mol per 1 mol of compound (III).

N,N-Diisopropylethylamine is used within the range of 1 mol to 2 mols per 1 mol of compound (III).

THF is used within the range of 1 mL to 50 mL per 1 g of compound (III).

The reaction temperature of Step 1 is generally −20° C. to 80° C., and the reaction time is about 0.5 hr to 15 hr.

After the completion of the reaction of Step 1, compound (V) can be isolated from the reaction mixture by extraction, washing with water and concentration.

Step 2 can be performed without solvent.

Sodium hydroxide is preferably in the form of fine particles, and used within the range of 1 mol to 5 mol per 1 mol of compound (V).

As the phase transfer catalyst, tetra-n-butylammonium hydrogensulfate is preferable and it is used within the range of 0.01 mol to 1 mol per 1 mol of compound (V).

The reaction temperature of Step 2 is generally 20° C. to 150° C., and the reaction time is about 0.5 hr to 24 hr.

After the completion of the reaction of Step 2, compound (I) can be purified by silica gel column chromatography, distillation under reduced pressure and the like.

4-2. Production Method 2

Production Method 2 is a production method of compound (I) which comprises Step 1 of reacting compound (III) with compound (IV) and Step 2 of reacting compound (V) in the presence of a base.

4-2-1. Step 1

Step 1 may be performed under any reaction conditions as long as compound (III) can be reacted with compound (IV) to give compound (V). Preferably, compound (III) is reacted with compound (IV) in the presence of an acid catalyst in a solvent or without solvent.

The compound (III) used in Step 1 is a known compound, and can be prepared by a method known per se. For example, as described in Bulletin of the Chemical Society of Japan, 1987, vol. 60, p. 397-398, it can be produced by ring opening of epihalohydrin with the corresponding halogenated hydrogen. Alternatively, a commercially available product can be used.

The compound (IV) used in Step 1 is a known compound, and can be prepared by a method known per se (e.g., a method described in Experimental chemical lecture (Maruzen) the 4th Edition, vol. 20, p. 245-248). Alternatively, a commercially available product can be used.

The amount of compound (IV) to be used is preferably 2 equivalents to 50 equivalents, more preferably 5 equivalents to equivalents, relative to compound (III). While the reaction can be carried out even when the amount of compound (IV) to be used is outside this range, when the amount is smaller than this range, the reaction does not proceed sufficiently and compound (III) tends to remain, and when the amount is greater than this range, an effect comparable to the amount of use cannot be provided, which tends to lead to industrial disadvantages.

The acid catalyst to be used in Step 1 is not particularly limited and, for example, p-toluenesulfonic acid, methanesulfonic acid, trifluoromethanesulfonic acid, sulfuric acid, hydrochloric acid, phosphoric acid, perchlorine acid, acidic ion exchange resin and the like can be mentioned, and p-toluenesulfonic acid, methanesulfonic acid and sulfuric acid are preferable.

The amount of the acid catalyst to be used is preferably 0.001 equivalent to 1 equivalent, more preferably 0.01 equivalent to 0.3 equivalent, relative to compound (III). While the reaction can be carried out even when the amount of the acid catalyst to be used is outside this range, when the amount is smaller than this range, the reaction tends to be slow, and when the amount is greater than this range, an effect comparable to the amount of use cannot be provided, which tends to lead to industrial disadvantages.

In Step 1, a metal halide may be further added to promote the reaction rate and, as the metal halide, lithium bromide, sodium bromide, zinc chloride, zinc bromide and the like can be mentioned, with preference given to lithium bromide. The amount of the metal halide to be used is preferably 0.05 equivalent to 10 equivalents, more preferably 0.5 equivalent to 5 equivalents, relative to compound (III).

Step 1 may be performed in a solvent that does not inhibit the reaction (e.g., single solvent of toluene, xylene, tetrahydrofuran, chlorobenzene, hexane and the like or a mixed solvent thereof), or preferably without solvent. When a solvent is used, its amount is preferably 1 L to 30 L per 1 kg of compound (III).

The reaction temperature of Step 1 is generally −20° C. to 120° C., preferably 10° C. to 70° C. The reaction time is generally 1 to 96 hr.

The compound (V) obtained in Step 1 can be isolated and purified by a conventional method. For example, the reaction mixture is neutralized where necessary with aqueous sodium hydrogencarbonate solution and the like, partitioned, dried and concentrated to isolate compound (V), which is further purified by, but not limited to, distillation under reduced pressure, silica gel column chromatography and the like. In addition, compound (V) can be subjected to Step 2 without purification.

The compound (V) obtained in Step 1 is useful as an intermediate for compound (I), and can also be used as an acetonylating reagent (see Journal of Organic Chemistry, 1986, vol. 51, p. 5425-5427).

4-2-2. Step 2

Step 2 can be performed, for example, by reacting compound (V) in the presence of a base in a solvent or without solvent to achieve dehydrohalogenation.

The base to be used in Step 2 is not particularly limited and, for example, inorganic bases such as potassium hydroxide, sodium hydroxide, cesium hydroxide, potassium carbonate, sodium carbonate, cesium carbonate and the like, organic bases such as triethylamine, tributylamine, diisopropylethylamine, 1,8-diazabicyclo[5.4.0]undece-7-ene (DBU), 1,5-diazabicyclo[4.3.0]non-5-ene (DBN), 1,4-diazabicyclo[2.2.2]octane (DABCO) and the like can be mentioned, with preference given to potassium hydroxide, sodium hydroxide and cesium hydroxide. The amount of the base to be used is preferably 0.9 equivalent to 5 equivalents, more preferably 1 equivalent to 2 equivalents, relative to compound (V). While the reaction can be carried out even when the amount of the base to be used is outside this range, when the amount is smaller than this range, the reaction does not proceed sufficiently and compound (V) tends to remain, and when the amount is greater than this range, side reactions may proceed.

When an inorganic base is used in Step 2, a phase transfer catalyst is preferably added to smoothly carry out the reaction by solubilizing the inorganic base. As the phase transfer catalysts, tetra-n-butylammonium hydrogensulfate, tetra-n-butylammonium bromide, tetra-n-butylammonium iodide and the like can be mentioned, with preference given to tetra-n-butylammonium hydrogensulfate. The amount of the phase transfer catalyst to be used is preferably 0.01 equivalent to 0.5 equivalent, more preferably 0.05 equivalent to 0.3 equivalent, relative to compound (V). While the reaction can be carried out even when the amount of the phase transfer catalyst to be used is outside this range, when the amount is smaller than this range, the reaction does not proceed sufficiently and compound (V) tends to remain, and when the amount is greater than this range, an effect comparable to the amount of use cannot be provided, which tends to lead to industrial disadvantages Step 2 may be performed in a solvent that does not inhibit the reaction (e.g., single solvent of toluene, xylene, tetrahydrofuran, chlorobenzene, hexane and the like or a mixed solvent thereof), or preferably without solvent. When a solvent is used, its amount is preferably 1 L to 30 L per 1 kg of compound (V).

The reaction temperature of Step 2 is generally 0° C. to 150° C. and preferably 20° C. to 100° C. The reaction time is generally 0.1 hr to 12 hr.

The compound (I) obtained in Step 2 can be isolated and purified by a conventional method (e.g., a method similar to that in Step 1), and preferably isolated and purified by the method described in Journal of Organic Chemistry, 1987, vol. 52, p. 3192-3196. To be specific, the reaction mixture is distilled under reduced pressure to give a fraction containing compound (I), which is diluted, where necessary, in a solvent (diethyl ether etc.), dried over anhydrous magnesium sulfate and the like, and concentrated to isolate and purify compound (I).

EXAMPLES

The present invention is explained in detail in the following by referring to Examples, which are not to be construed as limitative.

Example 1

Synthesis of 2-chloro-1-(chloromethyl)ethyl methoxymethyl ether 1,3-Dichloro-2-propanol (10.0 g, 77.5 mmol) was dissolved in dimethoxymethane (150 ml), lithium bromide (20.2 g, 232.5 mmol) and p-toluenesulfonic acid (1.33 g, 7.8 mmol) were added, and the mixture was stirred at room temperature for 3 days. After completion of the reaction, the reaction mixture was neutralized and partitioned with 5% aqueous sodium hydrogencarbonate solution (50 ml) and dried over anhydrous magnesium sulfate. Anhydrous magnesium sulfate was filtered off and the filtrate was concentrated to give a crude title compound (12.44 g). The crude title compound was distilled under reduced pressure (15 mmHg, 83° C.) to give a pure title compound (7.7 g, yield 57.5%).

$^1$H-NMR(CDCl$_3$, δppm) 3.43 (s, 3H), 3.69-3.77 (m, 4H), 3.99 (m, 1H), 4.76 (s, 2H)

Example 2

Synthesis of 2-(chloromethyl)-3,5-dioxahexa-1-ene

Potassium hydroxide (7.3 g, 130.0 mmol) and tetra-n-butylammonium hydrogensulfate (1.5 g, 4.3 mmol) were added to 2-chloro-1-(chloromethyl)ethyl methoxymethyl ether (15.0 g, 86.7 mmol), and the mixture was stirred at room temperature for 30 min. The mixture was heated to 80-90° C. and distilled under reduced pressure (20-30 mmHg, 50-55° C.). The obtained fraction (10.5 g) was dissolved in diethyl ether (50 ml) and dried over anhydrous magnesium sulfate. Anhydrous magnesium sulfate was filtered off and the filtrate was concentrated to give the title compound (9.3 g, yield 78.4%).

$^1$H-NMR(CDCl$_3$, δppm) 3.45 (s, 3H), 3.99 (s, 2H), 4.41 (s, 2H), 5.02 (s, 2H)

Example 3

Methoxymethyl Etherification of Methyl L-lactate

Methyl L-lactate (208 mg, 2 mmol) was dissolved in benzotrifluoride (2.0 mL), pyridinium p-toluenesulfonate (PPTS, 50 mg, 0.2 mmol) was added and then 2-(chloromethyl)-3,5-dioxahexa-1-ene (manufactured by Tokyo Kasei Kogyo Co., Ltd., 327 mg, 2.4 mmol) was added, and the mixture was stirred at room temperature for 24 hrs. Saturated aqueous sodium hydrogencarbonate solution (3 mL) was added to the reaction mixture, and the mixture was extracted with ethyl acetate (4 mL). The organic layer was washed with saturated aqueous sodium hydrogencarbonate solution (2 mL) and dried over anhydrous magnesium sulfate (0.5 g), and the solvent was evaporated under reduced pressure to give methyl (S)-2-(methoxymethoxy)propionate (248 mg, yield 84%).

$^1$H-NMR(CDCl$_3$, 400 MHz) δppm: 1.44 (3H, d, J=7 Hz), 3.39 (3H, s), 3.75 (3H, s), 4.24 (1H, q, J=7 Hz), 4.69 (1H, d, J=7 Hz), 4.70 (1H, d, J=7 Hz).

Example 4

Methoxymethyl Etherification of Methyl L-lactate

In the same manner as in Example 3 except that acetonitrile (2.0 mL) was used instead of benzotrifluoride, methyl (S)-2-(methoxymethoxy)propionate (256 mg, yield 86%) was obtained.

Example 5

Methoxymethyl Etherification of (S)-β-hydroxy-γ-butyrolactone

In the same manner as in Example 3 except that (S)-β-hydroxy-γ-butyrolactone (204 mg, 2 mmol) was used instead of methyl L-lactate and the reaction time was set to 15 hr, the corresponding (S)-β-(methoxymethoxy)-γ-butyrolactone (226 mg, yield 77%) was obtained.

$^1$H-NMR (CDCl$_3$, 400 MHz) δppm: 2.61 (1H, dd, J=18 Hz, J=3 Hz), 2.74 (1H, dd, J=18 Hz, J=6 Hz), 3.39 (3H, s), 4.36 (1H, dd, J=10 Hz, J=2 Hz), 4.42 (1H, dd, J=10 Hz, J=5 Hz), 4.48-4.52 (1H, m), 4.68 (2H, s).

Example 6

Methoxymethyl Etherification of Ethyl (S)-4-chloro-3-hydroxybutanoate

In the same manner as in Example 3 except that ethyl (S)-4-chloro-3-hydroxybutanoate (333 mg, 2 mmol) was used instead of methyl L-lactate and the reaction time was set to 15 hr, the corresponding ethyl (S)-4-chloro-3-(methoxymethoxy)butanoate (400 mg, 95%) was obtained.

$^1$H-NMR (CDCl$_3$, 400 MHz) δppm: 1.28 (3H, t, J=7 Hz), 2.66 (1H, dd, J=16 Hz, J=7 Hz), 2.72 (1H, dd, J=16 Hz, J=5 Hz), 3.40 (3H, s), 3.69 (2H, d, J=5 Hz), 4.16 (2H, q, J=7 Hz), 4.20-4.26 (1H, m), 4.70 (1H, d, J=7 Hz), 4.75 (1H, d, J=7 Hz).

Example 7

Methoxymethyl Etherification of Ethyl (S)-3-hydroxytetradecanoate

Ethyl (S)-3-hydroxytetradecanoate (2.00 g, 7.3 mmol) and 2-(chloromethyl)-3,5-dioxahexa-1-ene (manufactured by Tokyo Kasei Co., Ltd., 1.20 g, 8.8 mmol) were dissolved in THF (10 mL), p-toluenesulfonic acid (p-TsOH, 10 mg) was added, and the mixture was stirred at room temperature for 15 hr. Triethylamine (1 mL) was poured into the reaction mixture and the mixture was washed with saturated aqueous sodium hydrogencarbonate solution (10 mL) and saturated brine (10 mL), dried over anhydrous magnesium sulfate (0.5 g) and filtered. The solvent was evaporated to give the corresponding ethyl (S)-3-methoxymethoxytetradecanoate (2.20 g, yield 95%).

$^1$H-NMR (CDCl$_3$, 400 MHz) δppm: 0.88 (3H, t, J=7 Hz), 1.20-1.40 (18H, m), 1.47-1.60 (2H, m), 2.45 (1H, dd, J=15

Hz, J=5 Hz), 2.56 (1H, dd, J=15 Hz, J=7 Hz), 3.92-4.02 (1H, m), 4.14 (2H, q, J=7 Hz), 4.65 (1H, d, J=7 Hz), 4.68 (1H, d, J=7 Hz).

Example 8

Methoxymethyl Etherification of 1-phenylethanol p-Toluenesulfonic acid monohydrate (11.9 mg, 0.063 mmol) was added to a mixture of 1-phenylethanol (1.35 g, 12.5 mmol), 2-(chloromethyl)-3,5-dioxahexa-1-ene (2.05 g, 15.0 mmol) and acetonitrile (12.5 ml), and the mixture was stirred at room temperature for 4 hrs. The reaction mixture was poured into saturated aqueous sodium hydrogencarbonate solution (25 ml), and the mixture was extracted with ethyl acetate (25 ml). The organic layer was washed with saturated aqueous sodium hydrogencarbonate solution (25 ml) and dried over anhydrous magnesium sulfate (2.5 g). After filtration, the filtrate was concentrated under reduced pressure to give 1.74 g (yield 84%). The results are shown in Table 1.

Example 9

Methoxymethyl Etherification of 1-phenylethanol

In the same manner as in Example 8 except that pyridinium p-toluenesulfonate (314 mg, 1.25 mmol) was used instead of p-toluenesulfonic acid monohydrate and the reaction time was set to 54 hr, methoxymethyl 1-phenylethyl ether (1.77 g, yield 85%) was obtained. The results are shown in Table 1.

Examples 10-25

The same reactions as in Example 8 or 9 were carried out except that the hydroxyl group-containing compound, the acid catalyst and equivalent amount thereof (mol %) and reaction time were set to those shown in Table 1. The results (yields) are shown in Table 1. When the hydroxyl group-containing compound was primary alcohol (Examples 16-21) or tertiary alcohol (Examples 22-25), silica gel column chromatography or distillation under reduced pressure was employed for purification.

TABLE 1

| Example | hydroxyl group-containing compound | acid catalyst (equivalent mol %) | reaction time (h) | yield |
|---|---|---|---|---|
| 8 | OH / phenyl-CH(OH)-CH3 | p-TsOH (0.5 mol %) | 4 h | 84% |
| 9 | " | PPTS (10 mol %) | 54 h | 85% |
| 10 | OH / (S)-CH(OH)-COOMe | p-TsOH (0.5 mol %) | 2 h | 84% |
| 11 | " | PPTS (10 mol %) | 40 h | 86% |
| 12 | OH / Cl-CH2-CH(OH)-CH2-COOEt | p-TsOH (0.5 mol %) | 2 h | 94% |
| 13 | " | PPTS (10 mol %) | 32 h | 95% |
| 14 | cyclohexyl-CH(OH)-C≡CH | p-TsOH (0.5 mol %) | 2 h | 94% |
| 15 | " | PPTS (10 mol %) | 60 h | 98% |
| 16 | Ph-CH2-CH2-OH | p-TsOH (0.5 mol %) | 2 h | 51%[a] |
| 17 | " | PPTS (10 mol %) | 24 h | 44%[a] |
| 18 | HO-CH2-CH(CH3)-COOMe | p-TsOH (0.5 mol %) | 8 h | 52%[a] |
| 19 | " | PPTS (10 mol %) | 66 h | 59%[a] |
| 20 | HO-CH2-C(CH3)2-COOMe | p-TsOH (0.5 mol %) | 6 h | 59%[a] |
| 21 | " | PPTS (10 mol %) | 45 h | 72%[a] |
| 22 | HC≡C-C(OH)(CH3)-CH2-CH(CH3)2 | p-TsOH (0.5 mol %) | 12 h | 55%[a] |
| 23 | " | PPTS (10 mol %) | 88 h | 83%[a] |
| 24 | Ph-CH2-C(CH3)2-OH | p-TsOH (0.5 mol %) | 36 h | 55%[a] |
| 25 | " | PPTS (10 mol %) | 212 h | 57%[a] |

[a] purified by silica gel column chromatography or distillation under reduced pressure

INDUSTRIAL APPLICABILITY

A compound wherein the hydroxyl group of L-lactic acid is protected is, for example, useful as a raw material for an antifungal agent, a compound wherein the hydroxyl group of (S)-β-hydroxy-γ-butyrolactone or ethyl (S)-4-chloro-3-hydroxybutanoate is protected is, for example, useful as a raw material for an anti-AIDS drug or a therapeutic drug for hyperlipidemia, and a compound wherein the hydroxyl group of ethyl (S)-3-hydroxytetradecanoate is protected is, for example, useful as a raw material for an antiobesity agent.

This application is based on application Nos. 2003-288300 and 2004-79061 filed in Japan, the contents of which are hereby incorporated by reference in their entireties.

The invention claimed is:

1. A method of protecting a hydroxyl group, which comprises reacting a hydroxyl group-containing compound with a compound represented by the formula (I):

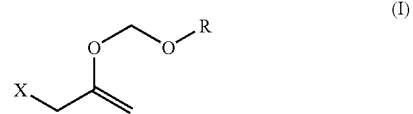

wherein R is a phenyl group optionally having substituent(s), an alkyl group optionally having substituent(s) or a benzyl group optionally having substituent(s), and X is a halogen atom, in the presence of an acid catalyst to substitute the hydrogen atom of the hydroxyl group of the hydroxyl group-containing compound with a protecting group represented by the formula (II):

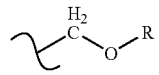
(II)

wherein R is as defined above.

2. The method of claim 1, wherein R is a phenyl group optionally having substituent(s) or an alkyl group optionally having substituent(s).

3. The method of claim 2, wherein R is an alkyl group.

4. The method of claim 1, wherein the acid catalyst is pyridinium p-toluenesulfonate or p-toluenesulfonic acid.

5. The method of claim 4, wherein the acid catalyst is pyridinium p-toluenesulfonate.

* * * * *